(12) United States Patent
Grass et al.

(10) Patent No.: US 9,867,584 B2
(45) Date of Patent: Jan. 16, 2018

(54) METHOD OF DETERMINING THE BLOOD FLOW THROUGH CORONARY ARTERIES

(71) Applicant: KONINKLIJKE PHILIPS N.V., Eindhoven (NL)

(72) Inventors: Michael Grass, Buchholz in der Nordheide (DE); Holger Schmitt, Luetjensee (DE); Hannes Nickisch, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 171 days.

(21) Appl. No.: 14/647,860

(22) PCT Filed: Nov. 21, 2013

(86) PCT No.: PCT/IB2013/060294
§ 371 (c)(1),
(2) Date: May 28, 2015

(87) PCT Pub. No.: WO2014/091339
PCT Pub. Date: Jun. 19, 2014

(65) Prior Publication Data
US 2015/0297161 A1 Oct. 22, 2015

Related U.S. Application Data

(60) Provisional application No. 61/735,624, filed on Dec. 11, 2012.

(51) Int. Cl.
*G06K 9/00* (2006.01)
*A61B 6/00* (2006.01)
(Continued)

(52) U.S. Cl.
CPC .............. *A61B 6/504* (2013.01); *A61B 6/032* (2013.01); *A61B 6/481* (2013.01); *A61B 6/482* (2013.01);
(Continued)

(58) Field of Classification Search
CPC . A61B 2090/3966; A61B 6/032; A61B 6/481; A61B 6/482; A61B 6/503;
(Continued)

(56) References Cited

U.S. PATENT DOCUMENTS 5,722,405 A 3/1998 Goldberg
7,627,080 B2 12/2009 Proksa
(Continued)

FOREIGN PATENT DOCUMENTS

DE 102008014792 6/2009
WO 2004025572 3/2004
(Continued)

OTHER PUBLICATIONS

Cerqueira, M. D., et al.; Standardized Myocardial Segmentation and Nomenclature for Tomographic Imaging of the Heart; 2002; Circulation; 105:539-542.
(Continued)

*Primary Examiner* — Manuchehr Rahmjoo

(57) ABSTRACT

A method of determining the blood flow through coronary arteries comprises generating (S1) a 3D image data set of at least the coronary arteries and the myocardial muscle, generating (S2) a 3D marker data set of at least the myocardial muscle from a dual-energy or spectral 3D data set obtained after administration of a marker, said 3D marker data set indicating the amount of said marker contained within voxels of said myocardial muscle, subdividing (S3) the myocardial muscle into myocardial muscle segments, determining (S4) which coronary artery supplies the respective
(Continued)

myocardial muscle segments, determining (S5) the volume of blood that flows into the respective myocardial muscle segments from said 3D marker data set, and determining (S6) the total volume of blood that flows into a coronary artery of interest by summing the volume of blood flowing into all myocardial muscle segments supplied by said coronary artery.

14 Claims, 5 Drawing Sheets

(51) Int. Cl.
  *G06T 7/00* (2017.01)
  *A61B 6/03* (2006.01)
  *A61B 90/00* (2016.01)

(52) U.S. Cl.
  CPC ............ *A61B 6/503* (2013.01); *A61B 6/5205* (2013.01); *A61B 6/5217* (2013.01); *A61B 90/39* (2016.02); *G06T 7/0012* (2013.01); *A61B 6/5288* (2013.01); *A61B 2090/3966* (2016.02); *G06T 2207/10081* (2013.01); *G06T 2207/30048* (2013.01); *G06T 2207/30104* (2013.01)

(58) Field of Classification Search
  CPC ..... A61B 6/504; A61B 6/5205; A61B 6/5217; A61B 6/5288; A61B 90/39; G06T 2207/10081; G06T 2207/30048; G06T 2207/30104; G06T 7/00
  See application file for complete search history.

(56) References Cited

U.S. PATENT DOCUMENTS

| | | | |
|---|---|---|---|
| 7,778,383 | B2 | 8/2010 | Koehler et al. |
| 8,157,742 | B2 | 4/2012 | Taylor |
| 8,200,466 | B2 | 6/2012 | Spilker |
| 8,249,815 | B2 | 8/2012 | Taylor |
| 8,386,188 | B2 † | 2/2013 | Taylor |
| 2010/0130878 | A1 | 5/2010 | Lasso |
| 2010/0241404 | A1 | 9/2010 | Taylor |
| 2011/0307231 | A1 | 12/2011 | Kirchner |
| 2012/0022843 | A1 | 1/2012 | Ionasec |
| 2012/0041318 | A1 | 2/2012 | Taylor |
| 2012/0041319 | A1 | 2/2012 | Taylor |
| 2012/0041320 | A1 | 2/2012 | Taylor |
| 2012/0041321 | A1 | 2/2012 | Taylor |
| 2012/0041322 | A1 | 2/2012 | Taylor |
| 2012/0041323 | A1 | 2/2012 | Taylor |
| 2012/0041324 | A1 | 2/2012 | Taylor |
| 2012/0041735 | A1 | 2/2012 | Taylor |
| 2012/0041739 | A1 | 2/2012 | Taylor |
| 2012/0053919 | A1 | 3/2012 | Taylor |
| 2012/0059246 | A1 | 3/2012 | Taylor |
| 2012/0072190 | A1 | 3/2012 | Sharma et al. |
| 2012/0121151 | A1 | 5/2012 | Bernhardt et al. |
| 2012/0243761 | A1 | 9/2012 | Senzig |
| 2016/0117816 | A1 † | 4/2016 | Taylor |

FOREIGN PATENT DOCUMENTS

| | | |
|---|---|---|
| WO | 2006061814 | 6/2006 |
| WO | 2006061815 | 6/2006 |
| WO | 2009077978 A1 | 6/2009 |
| WO | 2010022762 | 3/2010 |

OTHER PUBLICATIONS

Huo, Y., et al.; A validated predictive model of coronary fractional flow reserve; 2012; J. R. Soc. Interface; 9:1325-1338.
Itu, L., et al.; A patient-specific reduced-order model for coronary circulation; 2012; IEEE Int'l Symposium on Biomedical Imaging; pp. 832-835.
Kim, H. J., et al.; Patient-Specific Modeling of Blood Flow and Pressure in Human Coronary Arteries; 2010; Annals of Biomedical Engineering; 38(10)3195-3209.
Koo, B. K., et al.; Diagnosis of Ischemia-Causing Coronary Stenoses by Noninvasive Fractional Flow Reserve Computed From Coronary Computed Tomographic Angiograms; 2011; Journal of the American College of Cardiology; 58(19)1989-1997.
Koo, B. K.; Discover Flow (Diagnosis of Ischemia-causing Stenoses Obtained via Non-invasive Fractional Flow Reserve; 2011; the heart.org; Seoul National University Hospital, Korea; 3 pages.
Min, J. K., et al.; Rationale and design of the DeFACTO (Determination of Fractional Flow Reserve by Anatomic Computed Tomographic AngiOgraphy) study; 2011; Journal of Cardiovascular Computed Tomography; 5:301-309.
Sun, Q., et al.; Comprehensive validation of computational fluid dynamics simulations of in-vivo blood flow in patient-specific cerebral aneurysms; 2012; Medical Physics; 39(2)742-754.
Termeer, M., et al.; Patient-Specific Mappings between Myocardial and Coronary Anatomy; 1998; ACM Subject Classification 1.3.8 Applications, J.3 Life and Medical Sciences; pp. 196-209.
Wong, J. T., et al.; Quantification of fractional flow reserve based on angiographic image data; 2012; Int. J. Cardiovasc. Imaging; 28:13-22.

† cited by third party

METHOD OF DETERMINING THE BLOOD FLOW THROUGH CORONARY ARTERIES

CROSS REFERENCE TO RELATED APPLICATIONS

This application is a national filing of PCT application Serial No. PCT/IB2013/060294, filed Nov. 21, 2013, published as WO 2014/091339 A1 on Jun. 19, 2014, which claims the benefit of U.S. provisional application Ser. No. 61/735,624 filed Dec. 11, 2012, which is incorporated herein by reference.

FIELD OF THE INVENTION

The present invention relates to a method of determining the blood flow through coronary arteries. Further, the present invention relates to a corresponding processor, an imaging device and a computer program.

BACKGROUND OF THE INVENTION

Fluid dynamics calculations to estimate the stenosis related fractional flow reserve (FFR) based on single phase CT coronary angiography data sets are currently being evaluated in clinical studies. These calculations intend to deliver an additional functional parameter next to the spatial measurement of the degree of stenosis. The method is based on the segmentation of the coronary artery tree from a cardiac CT data set of a patient and subsequent simulation of blood flow velocity and pressure distribution in the vascular subsystem containing the stenosis.

The calculated quantity which is assumed to be clinically relevant is the fractional flow reserve, namely the pressure drop across a stenosis. The fluid dynamics calculations rely on different input data. In the first instance it is the geometry of the coronary arteries which determines the result of the flow simulation. However, other personalized boundary conditions like the blood flow velocity at the vessel inlet and/or the blood pressure may be important. The spatial dynamics of the coronary arteries due to the cardiac motion is currently neglected.

US 2012/0072190 A1 discloses a method and system for non-invasive patient-specific assessment of coronary artery disease. An anatomical model of a coronary artery is generated from medical image data. A velocity of blood in the coronary artery is estimated based on a spatio-temporal representation of contrast agent propagation in the medical image data. Blood flow is simulated in the anatomical model of the coronary artery using a computational fluid dynamics (CFD) simulation using the estimated velocity of the blood in the coronary artery as a boundary condition.

Further, Kim et al., Patient-Specific Modeling of Blood Flow and Pressure in Human Coronary Arteries, Annals of Biomedical Engineering, Vol. 38, No. 10, October 2010, pp. 3195-3209 discloses a method that predicts coronary flow and pressure of three-dimensional epicardial coronary arteries by considering models of the heart and arterial system and the interactions between the two models. For each coronary outlet, a lumped parameter coronary vascular bed model was assigned to represent the impedance of the downstream coronary vascular networks absent in the computational domain. The intramyocardial pressure was represented with either the left or right ventricular pressure depending on the location of the coronary arteries. The left and right ventricular pressure were solved from the lumped parameter heart models coupled to a closed loop system comprising a three-dimensional model of the aorta, three-element Windkessel models of the rest of the systemic circulation and the pulmonary circulation, and lumped parameter models for the left and right sides of the heart.

SUMMARY OF THE INVENTION

It is an object of the present invention to provide an efficient, accurate and reliable method of determining the blood flow through coronary arteries. It is a further object of the present invention to provide a corresponding processor, imaging device and computer program.

In a first aspect of the present invention a method of determining the blood flow through coronary arteries is presented that comprises the steps of generating a 3D image data set of at least the coronary arteries and the myocardial muscle, generating a 3D marker data set of at least the myocardial muscle from a dual-energy or spectral 3D data set obtained after administration of a marker, said 3D marker data set indicating the amount of said marker contained within voxels of said myocardial muscle, subdividing the myocardial muscle into myocardial muscle segments, determining which coronary artery supplies the respective myocardial muscle segments, determining the volume of blood that flows into the respective myocardial muscle segments from said marker data set, and determining the total volume of blood that flows into a coronary artery of interest by summing the volume of blood flowing into all myocardial muscle segments supplied by said coronary artery.

In a further aspect of the present invention a processor for determining the blood flow through coronary arteries is presented, said processor being configured to carry out the steps of the proposed method.

In still another aspect of the present invention an imaging device is presented comprising an acquisition unit for acquiring a dual-energy or spectral 3D data set, a processor as proposed herein for determining the blood flow through coronary arteries, and an output unit for outputting the determined total volume of blood that flows into a coronary artery of interest.

In yet further aspects of the present invention, there are provided a computer program which comprises program code means for causing a computer to perform the steps of the processing method when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed processor, imaging device, computer program and medium have similar and/or identical preferred embodiments as the claimed method and as defined in the dependent claims.

The invention is based on the idea to combine various kinds of information in a new way to obtain precise and reliable information about the blood flow through at least the coronary arteries. All said information can generally be derived from at least one 3D image data set of at least the coronary arteries and the myocardial muscle. An essential element of the proposed method hereby is to derive information on the volume of blood that flows into the respective myocardial muscle segments and to use this information for determining the total volume of blood that flows into a coronary artery. Further, in this approach an information is used about which artery (or arteries) is (are) connected with the respective myocardial muscle segments, which can be obtained in different ways, e.g. by use of a known AHA (American Heart Association) model (also called 17-segment model). The segmentation by use of such a model is e.g. described in Termeer M. et al., Patient-Specific Mappings between Myocardial and Coronary Anatomy, 1998 ACM Subject Classification 1.3.8 Applications, J.3 Life and Medical Sciences. It is also described there that the model can be individually adjusted which can also be used according to the present invention.

Said 3D marker data set of at least the myocardial muscle is generated from a dual-energy or spectral 3D data set that is obtained after administration of a marker. Said dual-energy or spectral 3D data set is preferably acquired by use of a dual-energy or spectral CT scanner. CT scans may provide additional boundary conditions which can be used in fluid dynamics simulations of blood flow in coronary arteries. This information is, for instance, integrated in a fluid dynamics simulation to increase its accuracy and to make the simulations more patient specific. Dual energy and spectral CT scans provide not only different levels of brightness, but also information about materials in the image and the concentration of materials. For example, bone and iodine can be separated although they both appear as bright pixels in standard CT images. Generally, however, other imaging modalities can be used that can quantify the amount of marker in a certain image area, e.g. MR, ultrasound or PET.

The administered marker, which is e.g. administered by injection, is preferably a contrast agent whose concentration within the tissue can be determined per voxel from said dual-energy or spectral 3D data set. Preferably, iodine-based or gadolinium based contrast agents are used.

According to an embodiment not only said 3D image data set of at least the coronary arteries and the myocardial muscle, but also the 3D marker data set of at least the myocardial muscle is generated from a dual-energy or spectral 3D data set acquired by use of a dual-energy or spectral CT scanner. Thus, in general the acquisition of only a single dual-energy or spectral 3D data set may be sufficient for deriving the 3D image data set and the 3D marker data set. Acquiring dual-energy or spectral 3D data set and deriving two different data sets there from is generally known in the art, in particular from the general publications relating to dual-energy or spectral CT (e.g. U.S. Pat. No. 7,627,080 B2 or U.S. Pat. No. 7,778,383 B2), and shall thus not be explained here in more detail.

According to a preferred embodiment that further enables to determine and/or simulate the volume of blood into the aorta the proposed method comprises the steps of determining the total volume of blood ejected by the heart during one cardiac cycle from said at least two 3D image data sets of the heart, wherein a first 3D image data set is obtained at a state of substantially maximal filling of the heart and a second 3D image data set is obtained at a state of substantially minimal filling of the heart, determining the total volume of blood that flows into all coronary arteries by summing the volume of blood flowing into all myocardial muscle segments, and determining the total volume of blood that flows into the aorta by subtracting the total volume of blood that flows into all coronary arteries from the total volume of blood ejected by the heart during one cardiac cycle.

This embodiment enables a flow simulation not only of the coronary arteries but also of the aorta which may be of interest in certain constellations.

According to another embodiment the proposed method further comprises the step of using said total volume of blood that flows into a coronary artery to determine the fractional flow reserve in or along said coronary artery. Thus, pressure drops across a stenosis can finally be determined by use of the present invention. The FFR value can thus be calculated at different locations within a coronary artery. Even further, for a coronary artery having two or more stenoses two or more FFR values can thus be calculated.

Preferably, said fractional flow reserve is determined by use of a computational fluid dynamics computation. Such a computational fluid dynamics (CFD) computation is commonly known in the art and e.g. described in detail in Qi, Sun: "Quantitative validation of CFD simulations of blood flow in cerebral aneurysms: in-vitro and in-vivo investigations" Sierke Verlag, 2012. Alternatively, an analytical pressure calculation model (as e.g. described in Huo Y. et al., A validated predictive model of coronary fractional flow reserve, J R Soc. Interface. 2012 Jun. 7; 9(71):1325-38. Epub 2011 Nov. 23) or a reduced order parameter model (as e.g. described in Itu, L. M. et al., A patient-specific reduced-order model for coronary circulation, IEEE, 2012, 832-835) can be used.

Advantageously, the myocardial muscle is subdivided into myocardial muscle segments by use of a 17-segment model, as e.g. described in Cerqueira M D, Weissman N J, Dilsizian V, Jacobs A K, Kaul S, Laskey W K, Pennell D J, Rumberger J A, Ryan T, Verani M S, "Standardized myocardial segmentation and nomenclature for tomographic imaging of the heart: a statement for healthcare professionals from the Cardiac Imaging Committee of the Council on Clinical Cardiology of the American Heart Association", Circulation, 2002, 105:539-542. The use of such model provides a good segmentation result. However, other segmentation algorithms or models for segmenting the myocardial muscle can be used alternatively, such as manual segmentation or manual delineation.

In an alternative embodiment the myocardial muscle is subdivided into myocardial muscle segments by use of patient-individual model and/or from at least one of said at least two 3D image data sets. The use of a patient-individual model increases the accuracy of the segmentation result and, thus, the result of the determining the blood flow through coronary arteries and the aortic arch.

According to another embodiment the volume of blood that flows into the respective muscle segments is determined from contrast agent uptake by the respective muscle segments in response to the administration of a contrast agent. For instance, a bolus of contrast agent can be observed to determine the volume of blood that flowing into a muscle segment.

Preferably, the cross sections and/or the resistance of coronary arteries is additionally used in the step determining the total volume of blood that flows into a coronary artery of interest. This helps to translate the volume over time entering the aorta in a volume per unit time entering each coronary artery that is e.g. selected for virtual FFR calculation.

A more advanced embodiment further comprises the steps of segmenting the left ventricle within said 3D image data sets, determining the total volume of blood ejected by the heart from the segmented left ventricle, determining the total volume of blood that flows into all coronary arteries by summing the volume of blood flowing into all myocardial muscle segments, and determining the total volume of blood that flows into the aorta by subtracting the total volume of blood that flows into all coronary arteries from the total volume of blood ejected by the heart during one cardiac cycle.

Still further, in an embodiment the method further comprises the steps of generating a plurality of 3D marker data sets of at least the myocardial muscle from a plurality of dual-energy or spectral 3D data sets obtained at consecutive times after said administration of said marker, determining the volume of blood that flows into the respective myocardial muscle segments over time from said plurality of 3D marker data set, determining the volume of blood that flows into a coronary artery of interest over time by summing the volume of blood flowing into all myocardial muscle segments supplied by said coronary artery at the respective consecutive times. Thus, the volume of blood that flows into a coronary artery of interest can be observed over time providing some potentially useful information.

Finally, in an embodiment the method further comprises the steps of generating a plurality of 3D marker data sets of at least the myocardial muscle, the coronary arteries and the heart from a plurality of dual-energy or spectral 3D data sets obtained at consecutive times after said administration of said marker and performing a fractional flow reserve simulation at a plurality of consecutive points in time.

Thus, a 4D marker data set can be obtained including FFR values over time.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
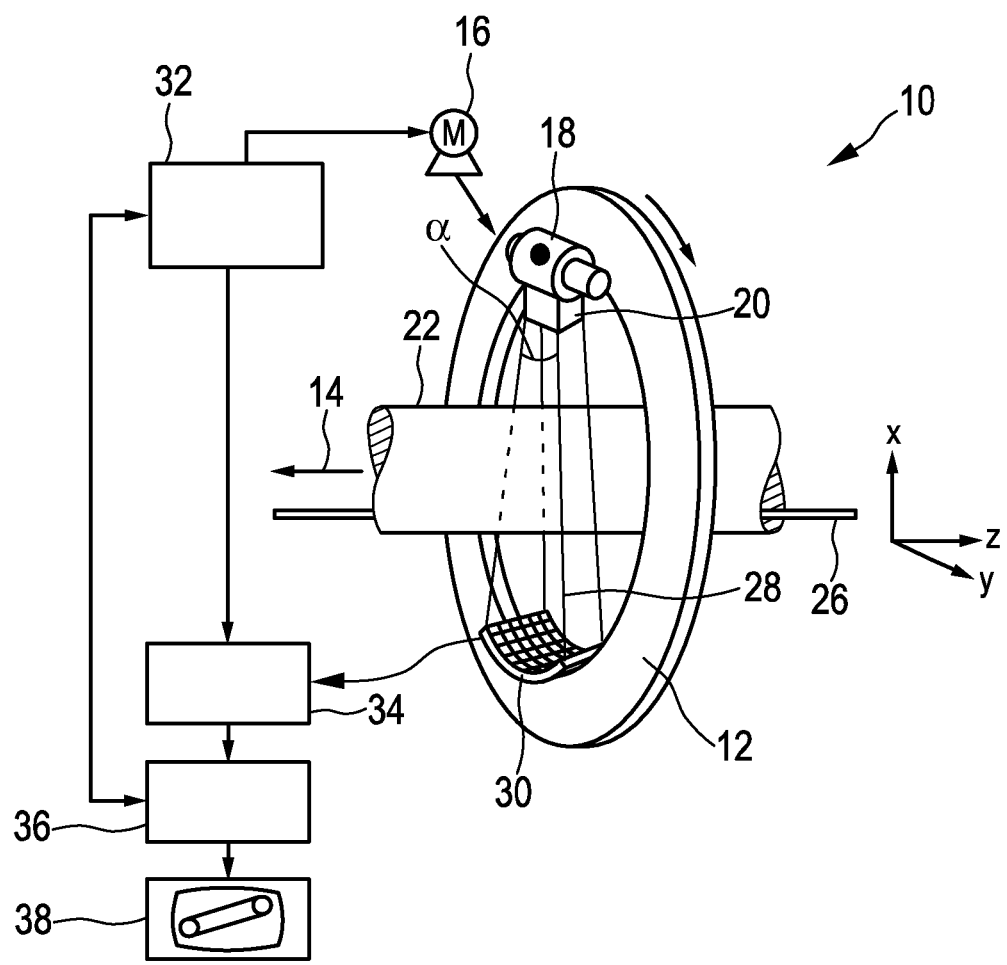
FIG. 1 shows an embodiment of an imaging device according to the present invention.

FIG. 1 shows an embodiment of an imaging device, here a computed tomographic (CT) system 10, according to the present invention. The CT system 10 includes a gantry 12 which is capable of rotation about an axis of rotation 14 which extends parallel to the z direction of the system of co-ordinates shown in FIG. 1. To this end, the gantry is driven at a preferably constant, but adjustable speed by a motor 16 that is controlled by a control unit 32. On the gantry there is mounted a radiation source 18, for example an X-ray source. This X-ray source is connected to a collimator arrangement 20 which, utilizing inter alia a diaphragm arrangement, forms a conical radiation beam 28 from the radiation produced by the radiation source 18, that is, a radiation beam 28 having a finite dimension other than zero in the direction of the z axis as well as in a direction perpendicular thereto (that is, in a plane perpendicular to the axis of rotation 14).

The radiation beam irradiates an examination zone 22 in which an object, for example a patient, arranged on a table top 26 of a patient table (not shown), may be situated. The examination zone 22 is shaped as a cylinder whose diameter is determined by the angle of aperture α of the radiation beam 28 (the angle of aperture is to be understood to mean the angle enclosed by a ray of the radiation beam 28 which is situated at the edge in a plane perpendicular to the axis of rotation 14 relative to the plane defined by the radiation source 18 and the axis of rotation).

After having traversed the examination zone 22, the X-ray beam 28 is incident on a two-dimensional detector 30 which is attached to the gantry 12 and comprises a plurality of detector rows, each of which comprises a plurality of detector elements. The detector rows are arranged in planes which are perpendicular to the axis of rotation 14, preferably on an arc of a circle around the radiation source 18. However, they may also be formed in a different way; for example, they may describe an arc of a circle around the axis of rotation 14 or be rectilinear. Each detector element that is struck by the radiation beam 28 supplies a measuring value for a ray of the radiation beam 28 in each position of the radiation source 18. Sets of such measuring values will also be referred to as projection data sets hereinafter. A projection data set comprises measuring values acquired by one or more detector elements at one or more projection angles. Projection data sets obtained from a number of different projection angles together form a 3D image data set, which can e.g. be used to reconstruct one or more images of the object (e.g. slice images from different perspectives).

The X-ray source 18 and the detector 30 together form an acquisition unit. The detector 18 generally also includes means for storing the acquired projection data. Such storage means may be included in the detector 30 or are (preferably) provided as an external separate storage unit 34 as shown in FIG. 1.

The examination zone 22, or the table top 26, can be displaced parallel to the axis of rotation 14, or parallel to the z axis, by means of a motor (not shown). The height of the table top 26 can be adjusted by means of another motor (not shown).

For processing the obtained 3D image data set(s) acquired by the acquisition unit a processing unit 36 is provided. The processing by said processing unit 36 will be explained in detail below. Reconstructed images or image portions may be displayed on a display unit 38, e.g. a computer monitor.

Figure 2:
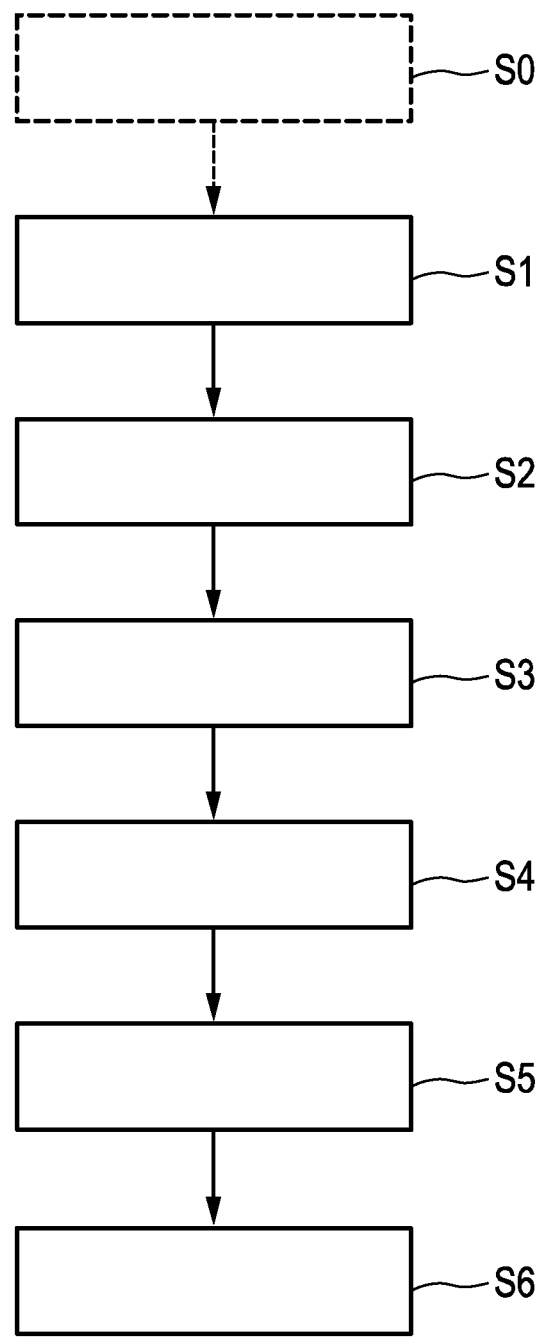
FIG. 2 shows a first embodiment of a method according to the present invention.
Figure 3A:
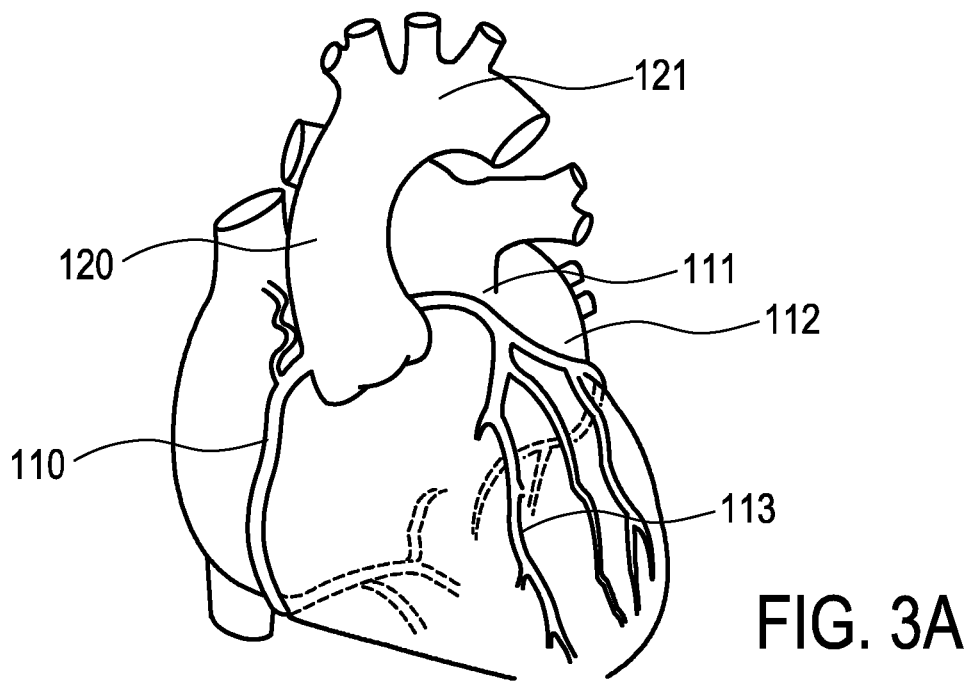
FIG. 3 shows schematic diagrams of the heart.
Figure 3B:
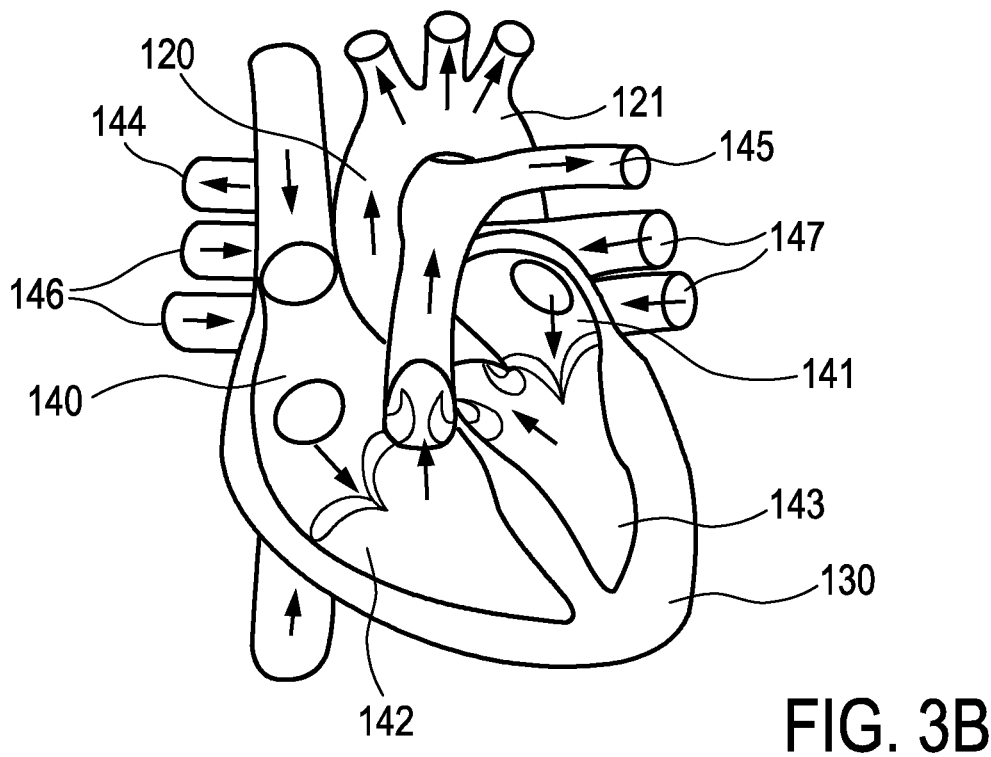

FIG. 2 shows a flow chart of a first embodiment of a method according to the present invention, particularly illustrating steps carried out by the processing unit 36 for determining the blood flow through coronary arteries. Schematic diagrams of the heart 100 are shown in FIG. 3, wherein FIG. 3A particularly shows the coronary arteries and the aortic arch and FIG. 3B particularly shows the heart muscle, the ventricles and the atriums.

The method carried out by the processing unit 36 receives as input a dual-energy or spectral 3D data set obtained after administration of a marker. Said dual-energy or spectral 3D data set can e.g. be obtained as an initial step S0 carried out by use of the acquisition unit. Alternatively, said dual-energy or spectral 3D data set can be stored in a database, i.e. can be acquired at an earlier point in time, and can now be provided as input to the method carried out by the processing unit 36.

In the first step S1 of the proposed method a 3D image data set of at least the coronary arteries and the myocardial muscle is generated. Preferably, the 3D image data set is generated from the input dual-energy or spectral 3D data set. However, the 3D image data set may generally be generated from a separate 3D data set acquired separately and/or at a different moment in time than said dual-energy or spectral 3D data set. The coronary arteries including the right coronary artery 110, the left main coronary artery 111, the circumflex coronary artery 112 and the left anterior descending coronary artery 113 are shown in FIG. 3A. The aorta 120 including the aortic arch 121 is shown in FIGS. 3A and 3B. The myocardial muscle 130 is shown in FIG. 3B. FIG. 3B further shows the right atrium 140, the left atrium 141, the right ventricle 142, the left ventricle 143, the right pulmonary artery 144, the left pulmonary artery 145, the right pulmonary vein 146 and the left pulmonary vein 147. The direction of the flow of blood is indicated in FIG. 3B by arrows.

In the second step S2 a 3D marker data set of at least the myocardial muscle is generated from a dual-energy or spectral 3D data set obtained after administration of a marker, said 3D marker data set indicating the amount of said marker contained within voxels of said myocardial muscle.

In step S3 the myocardial muscle 130 is segmented into myocardial muscle segments. This can, for instance, be done by a commonly known segmentation algorithm as commonly used in medical image processing, e.g. model-based or atlas-based segmentation. In a preferred embodiment the myocardial muscle is subdivided into myocardial muscle segments by use of a 17-segment model as proposed by the American Heart Association which subdivides the heart into 17 model segments as e.g. shown in the above cited paper of Termeer et al.

In step S4 it is determined which coronary artery supplies the respective myocardial muscle segments. This can, for instance, also be obtained by used of a 17-segment model and by assuming that coronary arteries and muscle segments lying in the same segment of the 17-segment model are coupled, i.e. the coronary artery in a model segment supplies the muscle segment arranged in the same model segment.

In step S5 the volume of blood that flows into the respective myocardial muscle segments from said 3D image data set is determined. This information can, for instance, be obtained from contrast agent uptake by the respective muscle segments in response to the administration of a contrast agent, which contrast agent uptake can be observed in 3D image data sets acquired over time.

In step S6 the total volume of blood that flows into a coronary artery of interest is determined by summing the volume of blood flowing into all myocardial muscle segments supplied by said coronary artery. For this purpose the cross sections and/or resistance of coronary arteries is preferably used in addition (for example by application of scaling laws as e.g. described in Huo Y. et al., A validated predictive model of coronary fractional flow reserve, J. R. Soc. Interface, doi:10.1098/rsif.2011.0605, published online) to increase the accuracy of this determination.

In the above explained embodiment a general model is used for segmenting the myocardial muscle into myocardial muscle segments. In an improved embodiment, in step S3 a patient-individual model is used which takes account of the actual form of the myocardial muscle of the actual patient. This improves the accuracy of the segmentation and, thus, of the whole method. In addition, also in step S4 the actual design of the myocardial muscle and/or the coronary arteries may be taken into account. The required information can e.g. be obtained from said 3D image data sets by use of an image segmentation, e.g. of the vessel tree.

In another preferred embodiment said 3D data set of the heart is acquired by use of a dual-energy or spectral CT scanner. This enables to derive a 3D data set showing different materials from the same measurement data. This can be used according to the present invention to obtain the 3D image data set and the 3D marker data set.

Figure 4:
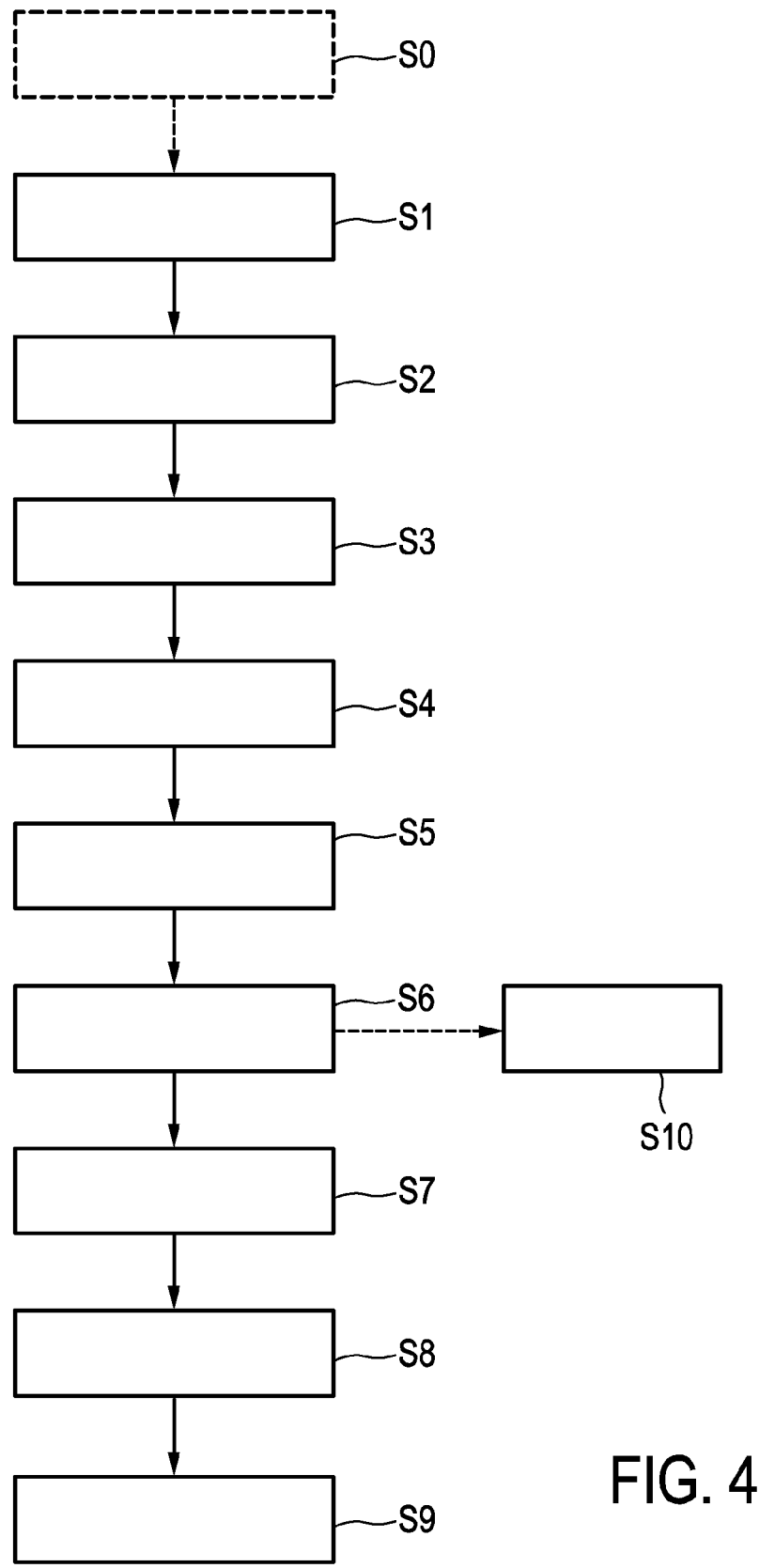
FIG. 4 shows a second embodiment of a method according to the present invention.

Another embodiment of the proposed method is schematically shown as flowchart in FIG. 4. This method comprises additional steps. In particular, in step S7 the total volume of blood ejected by the heart during one cardiac cycle from at least two 3D image data sets of the heart is determined, wherein a first 3D image data set is obtained at a state of substantially maximal filling of the heart and a second 3D image data set is obtained at a state of substantially minimal filling of the heart. Then, in step S8 the total volume of blood that flows into all coronary arteries is determined by summing the volume of blood flowing into all myocardial muscle segments (obtained as explained in step S5 for a myocardial muscle segment). Finally, in step S9 the total volume of blood that flows into the aorta is determined by subtracting the total volume of blood that flows into all coronary arteries from the total volume of blood ejected by the heart during one cardiac cycle.

In still another embodiment, indicated in FIG. 4 as an alternative path of an additional step, the total volume of blood that flows into a coronary artery (as determined in step S6) is used in step S10 to determine the fractional flow reserve in or along said coronary artery. Fractional flow reserve (FFR) is a technique used in coronary catheterization to measure pressure differences across a coronary artery stenosis (narrowing, usually due to atherosclerosis) to determine the likelihood that the stenosis impedes oxygen delivery to the heart muscle (myocardial ischemia). Fractional flow reserve is defined as the pressure behind (distal to) a stenosis relative to the pressure before the stenosis. The result is an absolute number; for instance, an FFR of 0.50 means that a given stenosis causes a 50% drop in blood pressure. In other words, FFR expresses the maximal flow down a vessel in the presence of a stenosis compared to the maximal flow in the hypothetical absence of the stenosis.

Preferably, said fractional flow reserve is determined in an embodiment by use of a computational fluid dynamics (CFD) computation. CFD is generally known as a method to calculate the 3D pressure and flow velocity distribution in given geometrical objects of almost arbitrary shape under given boundary conditions (e.g. fluid viscosity).

Figure 5:
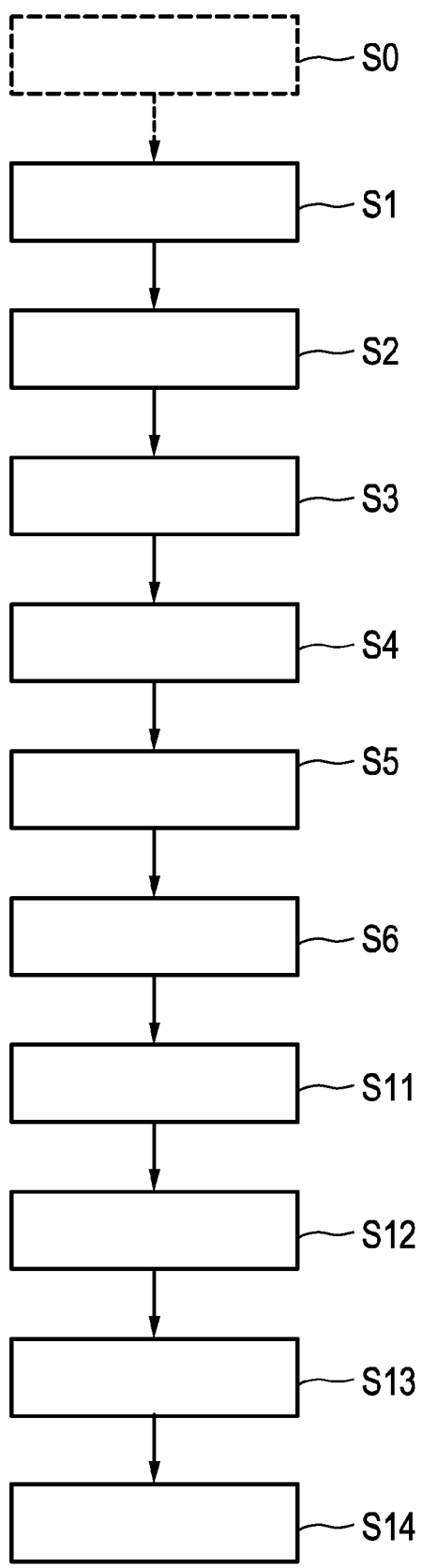
FIG. 5 shows a third embodiment of a method according to the present invention.

Still another embodiment of the proposed method is schematically shown as flowchart in FIG. 5. This method comprises additional steps. In particular, in step S11 the left ventricle 143 is segmented within said 3D image data sets. Then, in step S12 the total volume of blood ejected by the heart from the segmented left ventricle is determined, e.g. by use of the two 3D image data sets showing the heart in a state of maximal filling and minimal filling. In subsequent step S13 the total volume of blood that flows into all coronary arteries is determined by summing the volume of blood flowing into all myocardial muscle segments. Finally, in step S14 the total volume of blood that flows into the aorta 120 is determined by subtracting the total volume of blood that flows into all coronary arteries from the total volume of blood ejected by the heart during one cardiac cycle. Thus, additional information regarding the flow of blood can be easily obtained.

Generally, two different scenarios are feasible to estimate additional flow relevant parameters. In a first scenario information derived from 4D reconstructed image volumes is used. When using a 4D cardiac CT scan (e.g. ECG gated cardiac CT scan), or at least a biphasic acquisition protocol, two cardiac images corresponding to end systole and late diastole can be reconstructed. In these data sets, the left ventricular volume can be determined either by interactive segmentation or using a model-based segmentation process. The volume difference between the ventricle in end-systole and late diastole can be used to calculate the ejection fraction or dV/dt, which is the blood volume per unit time entering the left ventricular outflow tract (LVOT). When using a full 4D cardiac CT scan (e.g. ECG gated cardiac CT scan) the blood flow per unit time from the left ventricle in the left ventricular outflow tract can even be calculated in a time resolved fashion, delivering a dV/dt curve across the cardiac cycle as a start value for the fluid dynamics simulation.

In a second scenario information derived from 2D bolus tracking images is used. In addition to biphasic or multi-phase cardiac information, the contrast bolus arrival can be used to measure the blood volume over time entering the aorta. Usually the bolus arrival is measured for every cardiac CT scan in a single slice in the ascending aorta. Assuming a homogeneous contrast agent to blood mixture and a relatively compact cardiac output of the left ventricle in the aorta, the blood volume injected over time into the aorta is directly proportional to the contrast increase over time in the aortic slice. Sliding window reconstruction is required for a dense temporal sampling of the contrast increase of the aorta.

For both approaches, the volume over time entering the aorta is preferably translated in a volume per unit time entering each coronary artery selected for virtual FFR calculation. This can be achieved by using the different vessel cross sections taking up the blood from the ventricle, using the different vessel cross section and the resistance of the vessels taking up the blood from the ventricle, and/or a separate computational fluid dynamics calculation for the aortic trunk and the coronary vessels.

In still a further embodiment a plurality of 3D marker data sets of at least the myocardial muscle is obtained from a plurality of dual-energy or spectral 3D data sets obtained at consecutive times after said administration of said marker. Then, the volume of blood that flows into the respective myocardial muscle segments over time is determined from said plurality of 3D marker data set. This enables determining the volume of blood that flows into a coronary artery of interest over time by summing the volume of blood flowing into all myocardial muscle segments supplied by said coronary artery at the respective consecutive times.

Finally, in an embodiment a plurality of 3D marker data sets of at least the myocardial muscle, the coronary arteries and the heart is obtained from a plurality of dual-energy or spectral 3D data sets obtained at consecutive times after said administration of said marker. This enables performing a fractional flow reserve at a plurality of consecutive points in time.

Cardiac perfusion imaging is important for diagnosis and decision making in cases of coronary heart disease. Treatment is needed in cases where tissue perfusion is impaired. However, this quantity cannot be assessed directly as of today, because of the non-stationary nature of the beating heart. Embodiments of the proposed model-based reconstruction technique overcome this problem and can be used to reconstruct contrast agent uptake for specific myocardial regions. Derived quantities, for example bolus arrival time or time to peak enhancement, can be visualized in color coded images. Further, the blood flow through coronary arteries and the aortic arch of a heart can be reliably and easily measured.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A method of determining the blood flow through coronary arteries, comprising
   generating a 3D image data set of at least the coronary arteries and the myocardial muscle,
   reconstructing a 3D marker data set of at least the myocardial muscle from a dual-energy or spectral 3D projection data set generated by and obtained from one of a computed tomography, magnetic resonance, ultrasound or positron emission tomography imaging system after administration of a marker, said 3D marker data set indicating the amount of said marker contained within voxels of said myocardial muscle,
   subdividing in the 3D marker data set the myocardial muscle into myocardial muscle segments using a segmentation model,
   determining which coronary artery supplies the respective myocardial muscle segments by assuming that a coronary artery in a subdivided myocardial muscle segment supplies the myocardial muscle segment arranged in the same subdivided myocardial muscle segment,
   determining the volume of blood that flows into the respective myocardial muscle segments from said 3D marker data set, and
   determining the total volume of blood that flows into a coronary artery of interest by summing the volume of blood flowing into all myocardial muscle segments supplied by said coronary artery.

2. The method as claimed in claim 1, wherein said 3D image data sets of at least the coronary arteries and the myocardial muscle and the 3D marker data set of at least the myocardial muscle are generated from a dual-energy or spectral 3D data set acquired by use of a dual-energy or spectral CT scanner.

3. The method as claimed in claim 2, further comprising the step of acquiring said dual-energy or spectral 3D data set by use of a dual-energy or spectral CT scanner.

4. The method as claimed in claim 1, further comprising the steps of
- determining the total volume of blood ejected by the heart during one cardiac cycle from at least two 3D image data sets of the heart, wherein a first 3D image data set is obtained at a state of substantially maximal filling of the heart and a second 3D image data set is obtained at a state of substantially minimal filling of the heart,
- determining the total volume of blood that flows into all coronary arteries by summing the volume of blood flowing into all myocardial muscle segments, and
- determining the total volume of blood that flows into the aorta by subtracting the total volume of blood that flows into all coronary arteries from the total volume of blood ejected by the heart during one cardiac cycle.

5. The method as claimed in claim 1, further comprising the step of using said total volume of blood that flows into a coronary artery to determine the fractional flow reserve in or along said coronary artery.

6. The method as claimed in claim 5, wherein said fractional flow reserve is determined by use of a computational fluid dynamics computation, an analytical pressure calculation model or a reduced order parameter model.

7. The method as claimed in claim 1, wherein the myocardial muscle is subdivided into myocardial muscle segments by use of a 17-segment model.

8. The method as claimed in claim 1, wherein the myocardial muscle is subdivided into myocardial muscle segments by use of patient-individual model and/or from at least one of said at least two 3D image data sets.

9. The method as claimed in claim 1, wherein the cross section and/or the resistance of coronary arteries is additionally used in the step determining the total volume of blood that flows into a coronary artery of interest.

10. The method as claimed in claim 1, further comprising the steps of
- segmenting the left ventricle within said 3D image data set,
- determining the total volume of blood ejected by the heart from the segmented left ventricle,
- determining the total volume of blood that flows into all coronary arteries by summing the volume of blood flowing into all myocardial muscle segments, and
- determining the total volume of blood that flows into the aorta by subtracting the total volume of blood that flows into all coronary arteries from the total volume of blood ejected by the heart during one cardiac cycle.

11. The method as claimed in claim 1, further comprising the steps of
- generating a plurality of 3D marker data sets of at least the myocardial muscle from a plurality of dual-energy or spectral 3D data sets obtained at consecutive times after said administration of said marker,
- determining the volume of blood that flows into the respective myocardial muscle segments over time from said plurality of 3D marker data set,
- determining the volume of blood that flows into a coronary artery of interest over time by summing the volume of blood flowing into all myocardial muscle segments supplied by said coronary artery at the respective consecutive times.

12. The method as claimed in claim 1, further comprising the steps of
- generating a plurality of 3D marker data sets of at least the myocardial muscle, the coronary arteries and the heart from a plurality of dual-energy or spectral 3D data sets obtained at consecutive times after said administration of said marker and
- performing a fractional flow reserve simulation at a plurality of consecutive points in time.

13. A processor for determining the blood flow through coronary arteries, said processor being configured to
- generate a 3D image data set of at least the coronary arteries and the myocardial muscle,
- generate a 3D marker data set of at least the myocardial muscle from a dual-energy or spectral 3D data set generated by and obtained from one of a computed tomography, magnetic resonance, ultrasound or positron emission tomography imaging system after administration of a marker, said 3D marker data set indicating the amount of said marker contained within voxels of said myocardial muscle,
- subdivide in the 3D marker data set the myocardial muscle into myocardial muscle segments using a segmentation model,
- determine which coronary artery supplies the respective myocardial muscle segments by assuming that a coronary artery in a subdivided myocardial muscle segment supplies the myocardial muscle segment arranged in the same subdivided myocardial muscle segment,
- determine the volume of blood that flows into the respective myocardial muscle segments from said 3D marker data set, and
- determine the total volume of blood that flows into a coronary artery of interest by summing the volume of blood flowing into all myocardial muscle segments supplied by said coronary artery.

14. An imaging device comprising:
- an X-ray source and a detector that together provide an acquisition unit for acquiring a dual-energy or spectral 3D data set,
- the processor as claimed in claim 13 for determining the blood flow through coronary arteries, and
- a monitor for outputting the determined total volume of blood that flows into a coronary artery of interest.

* * * * *